(12) United States Patent
Baumann et al.

(10) Patent No.: US 7,614,786 B2
(45) Date of Patent: Nov. 10, 2009

(54) POSITIONING DEVICE FOR AN X-RAY DETECTOR

(75) Inventors: Heinz Baumann, Uttenreuth (DE); Thomas Engel, Erlangen (DE); Gerhard Friedrich, Altenstadt (DE); Martin Hecht, Erbendorf (DE); Peter Nögel, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 233 days.

(21) Appl. No.: 10/578,538

(22) PCT Filed: Nov. 3, 2004

(86) PCT No.: PCT/EP2004/052781

§ 371 (c)(1),
(2), (4) Date: Dec. 4, 2006

(87) PCT Pub. No.: WO2005/044106

PCT Pub. Date: May 19, 2005

(65) Prior Publication Data
US 2007/0183587 A1 Aug. 9, 2007

(30) Foreign Application Priority Data
Nov. 7, 2003 (DE) ................. 103 52 010

(51) Int. Cl.
*H05G 1/02* (2006.01)
(52) U.S. Cl. ...................... 378/195; 378/193
(58) Field of Classification Search .......... 378/189, 378/193, 195–197, 210
See application file for complete search history.

(56) References Cited

U.S. PATENT DOCUMENTS

| 5,410,584 | A | 4/1995 | Schaefer et al. |
| 5,432,834 | A | 7/1995 | Gershman |
| 5,466,249 | A * | 11/1995 | de Putter .................. 607/90 |
| 6,334,708 | B1 | 1/2002 | Kosugi |
| 6,428,206 | B1 * | 8/2002 | Watanabe ................ 378/197 |
| 6,461,039 | B1 | 10/2002 | Klotz et al. |

(Continued)

FOREIGN PATENT DOCUMENTS

| EP | 0 917 856 | 11/1998 |
| EP | 0 917 856 | 5/1999 |
| WO | WO 95/13017 | 5/1995 |
| WO | WO 03/032835 | 4/2003 |

OTHER PUBLICATIONS

International Search Report.
IPER with English Summary of the IPER dated Oct. 20, 2005.

*Primary Examiner*—Edward J Glick
*Assistant Examiner*—Anastasia Midkiff
(74) *Attorney, Agent, or Firm*—Brinks, Hofer, Gilson & Lione

(57) ABSTRACT

A positioning device for an X-ray detector or an X-ray source is provided. The positioning device includes an arched arm, inside of which the X-ray detector or the X-ray source can be mounted in a manner that enables the detector or source to be displaced in the direction of the arch. The positioning device includes a base, inside of which the arched arm is mounted in a manner that enables the arched arm to be displaced in the direction of the arch. Either the X-ray detector is mounted in the positioning device and the X-ray source is placed separately therefrom or, conversely, the X-ray source is mounted in the positioning device and the X-ray detector is placed separately there from.

7 Claims, 4 Drawing Sheets

U.S. PATENT DOCUMENTS

Figure 1:
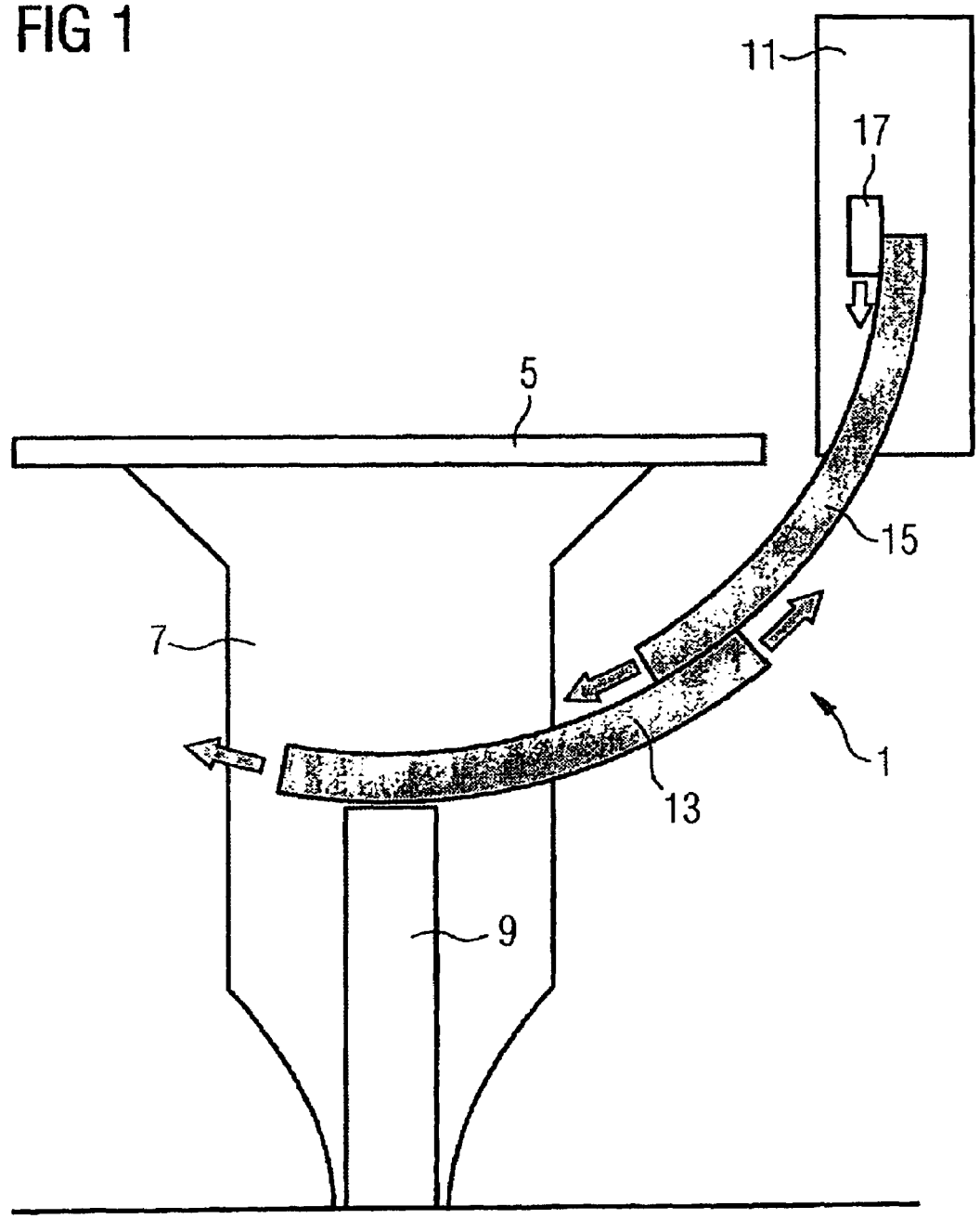

| | | | |
|---|---|---|---|
| 6,789,941 B1 * | 9/2004 | Grady | 378/197 |
| 7,170,972 B2 * | 1/2007 | Altman | 378/62 |
| 2003/0072416 A1 * | 4/2003 | Rasche et al. | 378/197 |
| 2003/0194051 A1 * | 10/2003 | Wang et al. | 378/37 |

* cited by examiner

POSITIONING DEVICE FOR AN X-RAY DETECTOR

BACKGROUND

1. Field

A positioning device for an X-ray detector and an X-ray source is provided.

2. Related Art

X-ray machines serve to take X-ray images, by means of an X-ray detector and an X-ray source. In the medical field, bodies or body parts of patients are X-rayed in various positions and from various directions for diagnosis purposes. Patient-support tables are used so the patient or body part can lie or sit while being examined.

In X-ray machines with patient-support tables, the X-ray detector is usually located under the tabletop, while an X-ray source X-rays the patient from above. A corresponding arrangement of X-ray sources and an X-ray detector can be achieved by using a so-called C-arm, for instance, which carries the sources and detector on diametrically opposed ends. This arrangement can also be achieved by means of a separate disposition of the X-ray detector in the patient-support table and of the X-ray source on a free-standing tripod or a tripod secured to the ceiling of the room.

To make different radioscopy directions possible, the X-ray source may be movably supported on a tripod in all directions in space. However, on a C-arm, the X-ray source is fixed and is movable solely by moving the C-arm itself. The X-ray detector is located on a C-arm and is always diametrically opposite the X-ray source. Thus, the X-ray detector is movable only to a limited extent as the patient-support device is being moved toward the X-ray detector.

Depending on where the X-ray machine is used, the freest possible adjustability of the radioscopy direction may be desired, for instance in radiation monitoring of interventional procedures in surgery or interventional cardiology. The radioscopy direction must be adjustable such that the various surgical steps are optimally visible in the X-ray projection. At the same time, the freest possible accessibility of the patient-supporting table and the patient lying on the table is of particular significance. C-arm X-ray machines are therefore often used in interventional use. While C-arm X-ray machines have advantages because of the particularly flexible (capable of various positions) capabilities of orientation, the C-arm is relatively bulky and hinders access to the patient. The size and arrangement of the C-arm limits the possibilities for using C-arm equipment.

From European Patent Disclosure EP 1 129 664, a patient-support table with a flexibly positionable X-ray detector is known. The X-ray detector is longitudinally displaceable under the tabletop of the device. The X-ray detector is also pivotable out of the device transversely to the longitudinal direction and can be tilted in such a way that X-ray detector is oriented perpendicular to the tabletop. When this patient-support device is used in combination with an X-ray source that is movable in all directions, various radioscopy directions can be flexibly set (adjusted), and the accessibility of a patient lying on the tabletop is not restricted by a C-arm. However, the variation of the radioscopy directions is not continuously adjustable in the same way as with a C-arm machine. Thus, a surgeon must accustom himself to the handling of the device and the X-ray images that can be made using the device.

SUMMARY

A positioning device for an X-ray detector which simultaneously assures flexible (various positions) adjustment of the radioscopy direction and easy access to a patient on the patient-support table is provided. An X-ray machine has such a positioning device.

A patient supporting device, with a positioning device located under the patient supporting device, for an X-ray detector or an X-ray source has an arched arm. The X-ray detector or X-ray source is supported displaceably in the direction of the arch and has a base with an arched arm supported displaceably in the direction of the arch. The use of an arched arm enables the flexible adjustability to various positions of the radioscopy direction in the same way as would be done with a C-arm. For the surgeon, this has the advantage that he can adjust the radii of motion and radioscopy angles in the way that is familiar and customary.

The movability of the X-ray detector or the X-ray source on the arched arm, however, simultaneously increases range of motion in comparison with a C-arm, on which the X-ray detector and the X-ray source are secured nondisplaceably. As a result, to make a comparable range of motion possible, the arm can be reduced to half the length, compared to a C-arm arm. This reduces bulk, and there is less hindrance to access the patient-support device. The displaceability on a circular path, in combination with an X-ray source or X-ray detector located separate from the positioning device and displaceable on a contrarily extending circular path, makes it possible to create images of slices or three-dimensional images of the body to be examined. Such images of the body have generally been made using C-arm X-ray machines whose image data is processed into three-dimensional images by analogy with computed tomography image data. The prerequisite for this is the motion along a circular path whose center point is located in the body region to be examined.

In an advantageous feature, the arched arm is supported displaceably in the direction of the arch on a second arched arm, and the second arched arm is supported in the base displaceably in the direction of the arch. By using a second displaceable arm, the range of motion of the X-ray detector can be doubled, without having to increase the length of each individual arched arm substantially. Thus, a greater range of motion is attained while the bulk of the positioning device remains the same, and the accessibility to the patient-support device is not additionally hindered.

In a further advantageous feature, the X-ray detector or the X-ray source can be supported movably in the arched arm in the radial direction relative to the arch. As a result, the X-ray detector or the X-ray source can, as needed, be brought closer to a patient positioned in the center of the arch. This is especially advantageous if the positioning device is located under the patient-support table. If an X-ray detector is supported in the positioning device, the X-ray detector can be brought from below, toward the patient-support table so that an X-ray can be made with a vertical angle of incidence of the X-radiation. In this arrangement, X-ray images can be made that are possible with conventional X-ray machines that have an X-ray detector under the table, known as a Bucky system. This expands the possibilities for using the X-ray machine.

In a further advantageous feature, the positioning device is used in an X-ray machine with a patient-support device, and the X-ray machine has an X-ray source that is movably supported in all directions and is located separately from the positioning device. This configuration, because of the separate disposition of the X-ray source, allows free accessibility to the patient-support table because the positioning device does not substantially restrict accessibility. In addition, the X-ray source can be positioned to present as little hindrance as possible. Because of the free movability of the X-ray source, arbitrary angles of incidence can be set (adjusted). The X-ray source can for instance be supported from a ceiling-mounted tripod that allows increased accessibility to the patient-support table.

In a further advantageous feature, the X-ray machine has a control unit that is connected to the X-ray source and the positioning device. The control unit moves the X-ray source and the positioning device together, so that they assume a predetermined orientation relative to each other. The predetermined orientation can be selected such that the X-ray detector is at all times located in the X-ray beam of the X-ray source and perpendicular to the X-ray beam. This orientation makes it possible to create an X-ray image at all times without a machine operator having to manually adjust the various individual positions of each device. For example, if the X-ray source is aimed by a machine operator in a desired way, the X-ray detector automatically follow the motion using the control unit. The control unit can also be used to make three-dimensional or slice images of the body to be examined, where the X-ray source and the X-ray detector must be moved along a circular path, diametrically opposite one another.

DRAWINGS

Figure 2:
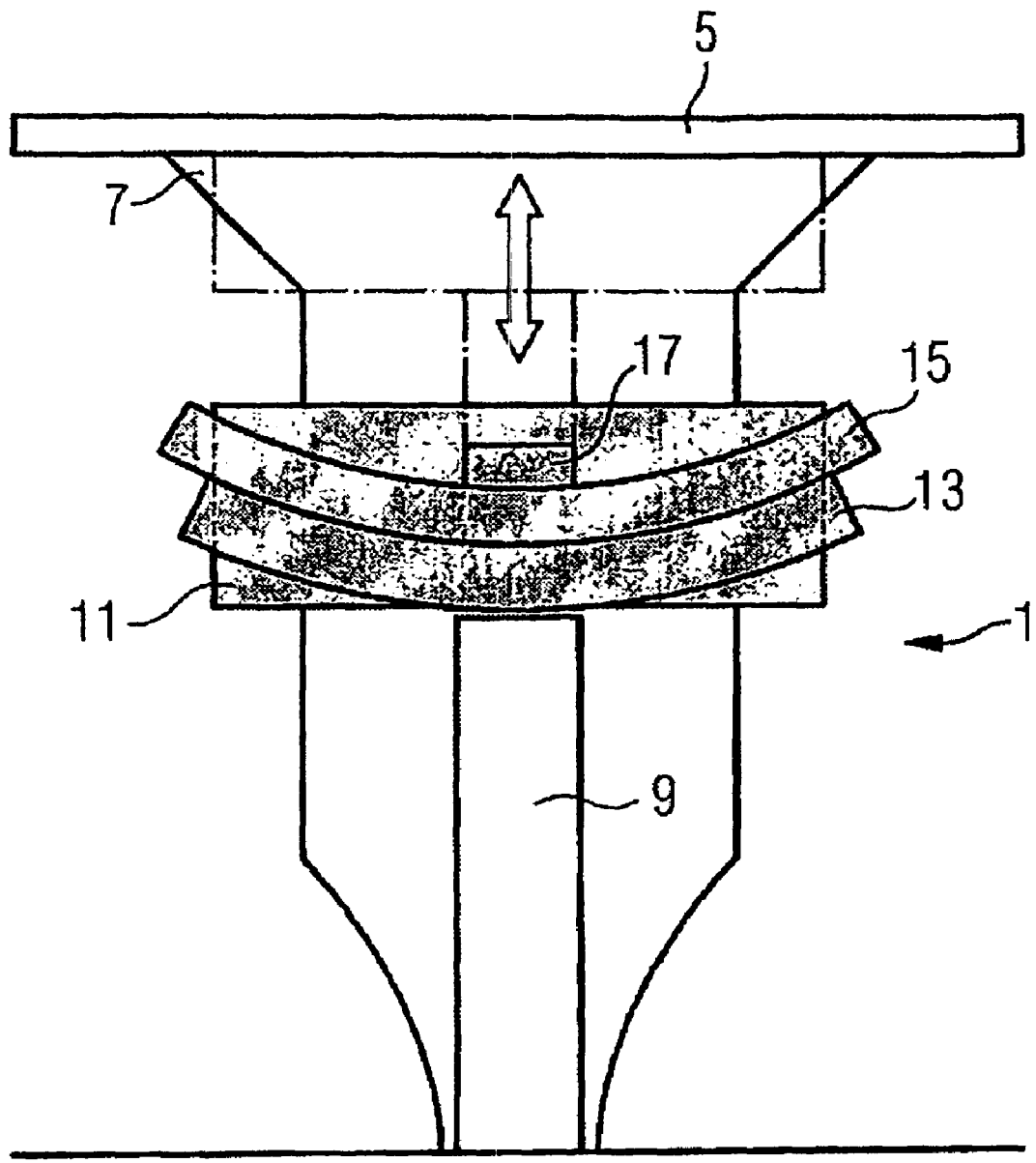
Figure 3:
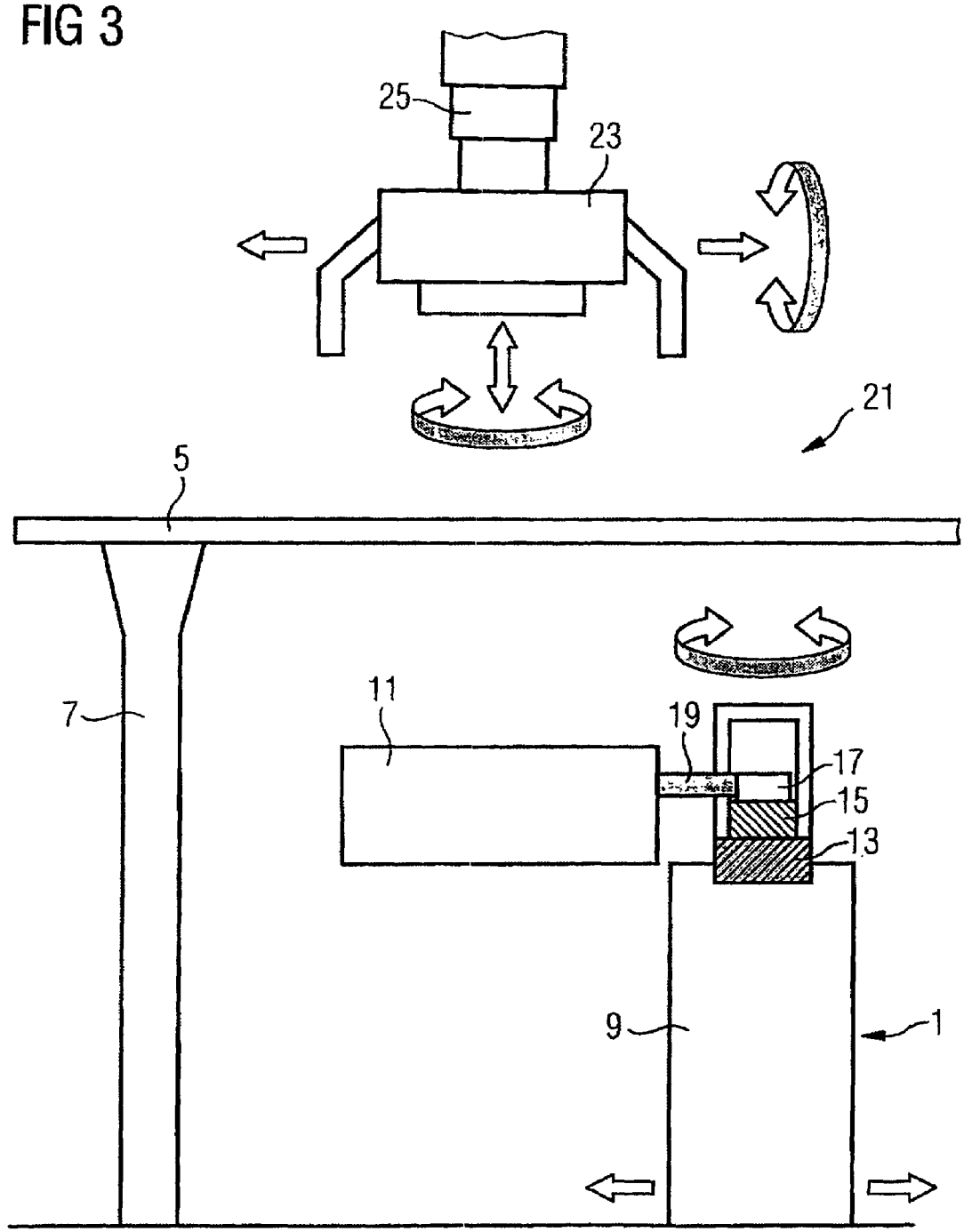

Exemplary embodiments are described in further detail below in conjunction with drawings. Shown in the drawings are:

FIG. 1, a positioning device with an X-ray detector and a patient-support device;

FIG. 2, the positioning device in a different position of the X-ray detector;

FIG. 3, an X-ray machine with a positioning device; and

Figure 4:
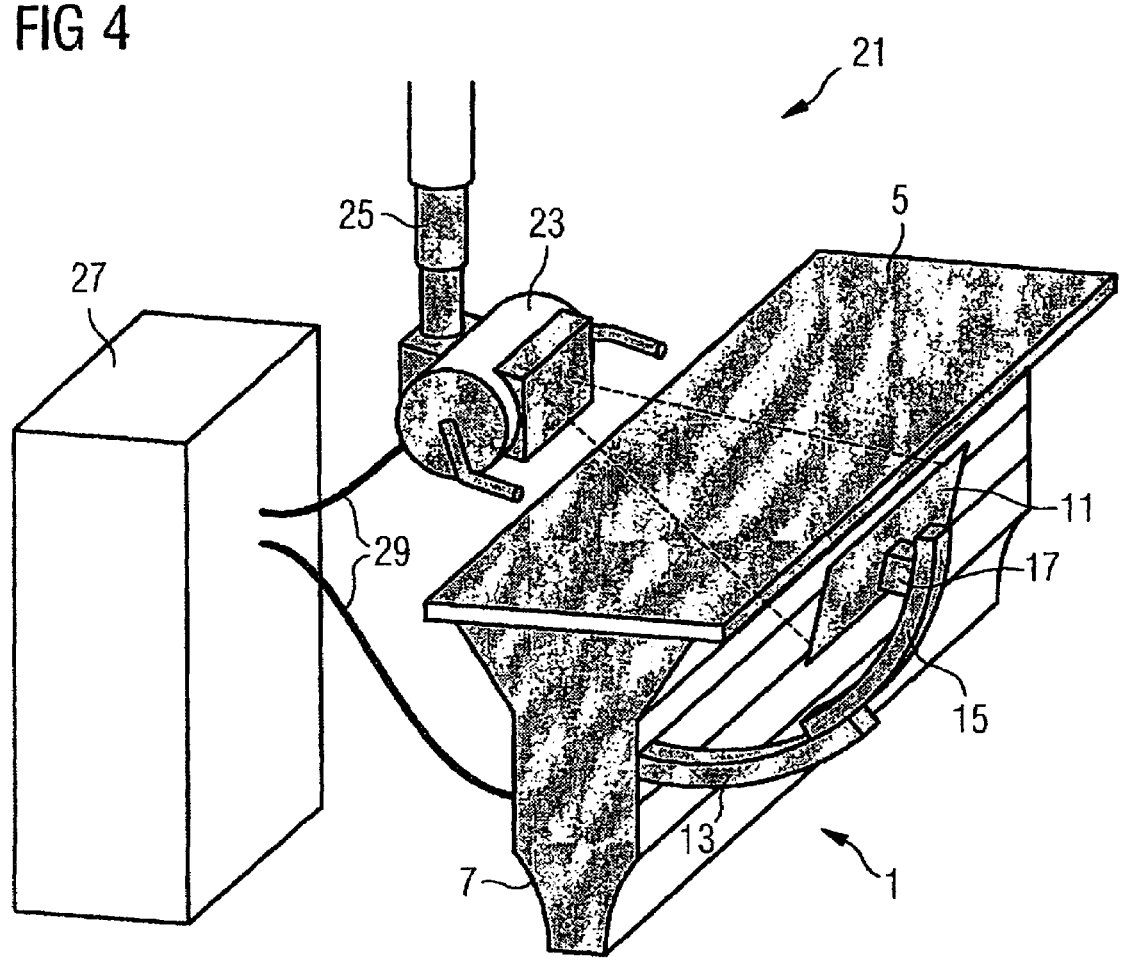

FIG. 4, an X-ray machine with a positioning device and a control unit.

DESCRIPTION

In FIG. 1, one embodiment of the positioning device 1 is shown along with a patient-support device. The patient-support device comprises a patient-support table 5, which is secured to a table pedestal 7.

The positioning device 1 is located under the patient-support table 5. It has a base 9 that is supported either on the patient-support device or on the floor.

An arched arm 15 is supported in the base 9 via a second arched arm 13. An X-ray detector 11 is supported on the arm 15 by a mounting device 17.

The mounting device 17 is movably supported in the arm 15 such that the X-ray detector 11 is displaceable along the arm 15 in the direction of the arch. In FIG. 1, the X-ray detector 11 is extended counterclockwise, compared to the outset position. From that position, the X-ray detector 11 can now be displaced clockwise, which is represented in the drawing by an arrow pointing clockwise. In this direction, it can be displaced as far as the diametrically opposed maximally deflected position, without being hindered by other device elements, such as an X-ray source, since it is the only part of the device that is supported on the arm 15.

The arched arm 15 is supported by the second arched arm 13 and is displaceable in the direction of the arch. The arched arm 15 is likewise located in a position that is maximally deflected counterclockwise. The arm 15 can likewise be displaced in the clockwise direction, which is represented by a corresponding arrow in the drawing.

The second arched arm 13 is supported in the base 9 and is displaceable in the direction of the arch. However, in contrast to the X-ray detector 11 and the arm 15, the second arched arm 13 is not located in a maximally deflected position and is therefore displaceable both clockwise and counterclockwise, which is also represented by corresponding arrows in the drawing.

In a first embodiment, the deflection of the X-ray detector 11 that is supported in the positioning device 1 can be adjusted by manual displacement operated by a machine operator. Bearing and locking mechanisms, not shown in the drawing, assure free movability and fixability in the desired deflection. In another embodiment, the deflection of the X-ray detector 11 can be motor-adjusted by the positioning device 1. In this embodiment, drive motors (not shown) automatically displace the arms 13, 15 and the mounting device 17 outward.

As shown in FIG. 2, the same positioning device 1 with a patient-support device 5, and the same reference numerals as in the preceding drawing are used. However, the arched arms 13, 15 and the mounting device 17 with the X-ray detector 11 are located in their outset position symmetrically to the base 9. In this position, the positioning device 1 has minimal bulk and allows machine operators or medical professionals to easily access the patient-support device 5.

In a another embodiment of the positioning device 1, the X-ray detector 11 is supportable on the arched arm 15 in a way that the X-ray detector 11 can be moved in the radial direction relative to the arch and toward the patient table 5. This motion is illustrated in FIG. 2 by a vertical arrow. The mounting device 17 that is supported movably in the direction of the arch in the arm 15 and is radially adjustable. The X-ray detector 11 that is held by the mounting device 17 can be brought closer to a patient located in the center of the arch. In this embodiment, the positioning device 1 is located under the tabletop 5. The X-ray detector 11 can be brought toward the tabletop 5, which is represented by dashed lines in FIG. 2. This arrangement is similar to that of an X-ray machine in which the X-ray detector is attached immediately under the table 5 either fixedly or movably in the longitudinal direction and is exposed vertically from above. Generally, this type of arrangement is called a Bucky system. Because of the radial movability of the X-ray detector 11, the positioning device 1 can therefore also be used as a Bucky system.

In FIG. 3, an X-ray machine 21 with a positioning device 1 is shown. The positioning device 1 has an arched arm 15 and a second arched arm 13. An X-ray detector 11 is supported as described above in a base 9, displaceable on a circular arc. The X-ray detector 11 is supported in the arm 15 via a supporting arm 19 and a mounting device 17. The positioning device 1 is located below a patient-support device that comprises a tabletop 5 supported on a table pedestal 7.

Located above the patient-support device is an X-ray source 23, which is supported in a ceiling-mounted tripod 25. The X-ray source 23 is movable in the vertical and horizontal directions, as indicated by corresponding arrows. Moreover, the X-ray source 23 may rotate about a horizontal axis and about a vertical axis, which is also indicated by arrows. Because of the three-dimensional movability of the X-ray source 23, virtually all arbitrary X-ray angles can be set.

The positioning device 1, because of its movability, assures that the X-ray detector 11 can be oriented in a way that adapts virtually all X-ray angles. In other words, the X-ray detector is oriented both in the X-ray beam and vertically to the X-ray beam. As shown by the arrows in FIG. 3, the X-ray detector 11 may rotate about a vertical axis. Accordingly, the X-ray detector 11 is supported rotatably on the supporting arm 19, or the supporting arm 19 is supported rotatably on the arm 15, or the arm 13 is rotatable in the base 9. The maximum settable angle of rotation depends on the construction, which is adapted to the particular use. In one embodiment, the settable angle of rotation amounts to at least 20°. Because of the free movability of the X-ray source 23 and the X-ray detector 11, virtually all arbitrary radioscopy angles for examining a patient (not shown) lying on the tabletop 5 can be attained.

In FIG. 4, an X-ray machine 21 with a positioning device 1, an X-ray source 23, and a control unit 27 are shown in perspective. The positioning device 1 has a base 9 that has arched arms 13, 15. The X-ray detector 11 is supported displaceably and movably on a mounting device 19. The mode of operation of the positioning device 1 corresponds to that described in the foregoing drawings.

The X-ray source 23 is supported three-dimensionally movably on a ceiling-mounted tripod 25 and likewise, as described above, is movable in the horizontal and vertical directions and is rotatable about a horizontal and a vertical axis.

The three-dimensional movability of the X-ray source 23 and of the X-ray detector 11 makes it possible to set (adjust) various radioscopy directions. The X-ray detector 11, for making an X-ray image, is located in the X-ray beam of the X-ray source 23 that is represented by dashed lines in the drawing, and vertically to it.

As shown in FIG. 4, the X-ray machine 21 has a control unit 27. The X-ray source 23 is connected to the control unit 27 via an electrical cord 29. Accordingly, both the generation of X-radiation and the motion of the X-ray source 23 can be controlled by the control unit 27. The positioning device 1 with the X-ray detector 11 is also connected to the control unit 27 via a cord 29. Thus, the motion of the positioning device 1 can be controlled by the control unit 27, and image data from the X-ray detector 11 can be transmitted.

The control unit 27 has a control program that controls the motion of the X-ray source 23 and of the positioning device 1. In one embodiment, the control program is designed such that the X-ray source 23 can be oriented manually by a machine operator. From position detectors (not shown), the control unit 27 receives information about the present position of the X-ray source 23 and triggers the positioning device 1 in such a way that the X-ray detector 11 follows along with the motions of the X-ray source 23. In a another embodiment, the control program of the control unit 27 is designed so the X-ray detector 11 and the X-ray source 23 move along a circular path, diametrically opposite of each other, around a patient (not shown) lying on the tabletop 5. X-ray image data, recorded in various X-ray beam directions along such a circular path, are processed to make three-dimensional images or images of slices of the body that is examined. The processing of the image data is done in a way similar to computed tomography, or in a way that image data is processed by a C-arm X-ray machine. The control unit 27 thus controls the X-ray source 23 and the positioning device 1 in such a way that the motion of a C-arm X-ray machine is simulated.

Operating the X-ray detector 11 in combination with the positioning device 1 described above allows a digital X-ray detector, such as a solid-state detector, to be used. Accordingly, X-ray image data is available immediately after the images are made. This is especially advantageous in interventional medical applications.

Embodiments of the positioning device 1 may have only one or a plurality of arched arms, with a corresponding mode of operation. For example, other versions of the X-ray machine 21 may have a wall-mounted or floor-mounted tripod, instead of a ceiling-mounted tripod 25. A version in which the positioning device 1 is embodied such that instead of an X-ray detector it has an X-ray source, and in which the X-ray detector is instead located separately from the positioning device 1, is also possible.

The invention claimed is:

1. An X-ray machine comprising
a patient-support device comprising:
an arched arm; and
a base,
wherein an X-ray detector or an X-ray source is supported on the arched arm and displaceable in the direction of the arch of the arched arm,
wherein the arched arm is supported by the base and is displaceable in the direction of the arch of the arched arm; and
the other of the X-ray detector or the X-ray source supported movably in all directions in space and located separately from the patient-support device.

2. The X-ray machine according to claim 1, wherein the patient-support device further comprises a positioning device, wherein the X-ray machine has a control unit that is connected to the X-ray source and the positioning device,
wherein the control unit is embodied so as to move the X-ray source and the positioning device in a manner adapted to one another, so that they assume a predetermined orientation to one another.

3. The X-ray machine as defined by claim 1, which has a control unit that is connected to the X-ray detector and the patient-support device,
wherein the control unit is embodied so as to move the X-ray detector and the patient-support device in a manner adapted to one another, so that they assume a predetermined orientation to one another.

4. The X-ray machine as defined by claim 1,
wherein the arched arm is supported in a second arched arm and displaceable in the direction of an arch of the second arched arm; and
wherein the second arched arm is supported in the base and is displaceable in the direction of the arch of the second arched arm.

5. The X-ray machine as defined by claim 1, wherein the patient-support device further comprises a patient-support table.

6. The X-ray machine as defined by claim 5, wherein the patient-support device further comprises a positioning device located underneath the patient-support table.

7. The X-ray machine according to claim 6, wherein the positioning device further comprises a control unit that is connected to the X-ray source and the positioning device, wherein the control unit is operable to move the X-ray source and the positioning device in a manner adapted to one another, so that the X-ray source and the positioning device assume a predetermined orientation to one another.

* * * * *